(12) United States Patent
Fleury et al.

(10) Patent No.: US 10,130,498 B2
(45) Date of Patent: Nov. 20, 2018

(54) STENT WITH FLEXIBLE HINGE

(71) Applicant: BOSTON SCIENTIFIC SCIMED, INC., Maple Grove, MN (US)

(72) Inventors: Sean P. Fleury, Brighton, MA (US); Dane T. Seddon, Boston, MA (US); Jason Weiner, Grafton, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 32 days.

(21) Appl. No.: 14/919,697

(22) Filed: Oct. 21, 2015

(65) Prior Publication Data

US 2016/0113789 A1 Apr. 28, 2016

Related U.S. Application Data

(60) Provisional application No. 62/067,039, filed on Oct. 22, 2014.

(51) Int. Cl.
*A61F 2/07* (2013.01)
*A61F 2/06* (2013.01)
(Continued)

(52) U.S. Cl.
CPC .................. *A61F 2/89* (2013.01); *A61F 2/88* (2013.01); *A61F 2/915* (2013.01); *A61F 2/848* (2013.01);
(Continued)

(58) Field of Classification Search
CPC .......... A61F 2/915; A61F 2/2418; A61F 2/07; A61F 2002/91583; A61F 2/844;
(Continued)

(56) References Cited

U.S. PATENT DOCUMENTS

| | | | |
|---|---|---|---|
| 4,994,071 A | | 2/1991 | MacGregor |
| 5,591,197 A | * | 1/1997 | Orth .......................... A61F 2/07 606/191 |

(Continued)

FOREIGN PATENT DOCUMENTS

| | | |
|---|---|---|
| EP | 0 732 088 A2 | 9/1996 |
| JP | 2007512114 A | 5/2007 |

(Continued)

*Primary Examiner* — Ann Schillinger

(74) *Attorney, Agent, or Firm* — Seager, Tufte & Wickhem, LLP

(57) ABSTRACT

An endoprosthesis may include an expandable tubular framework expandable from a compressed state to an expanded state and include a plurality of strut rows, wherein adjacent strut rows define interstices spacing the adjacent strut rows apart, and a plurality of connectors extending across the interstices and interconnecting adjacent strut rows, at least some of the plurality of connectors defining a flexible hinge portion. The lengths of the interstices between adjacent strut rows may vary along the length of the expandable tubular framework. The plurality of connectors extend radially outward beyond an outer diameter of the plurality of strut rows in the expanded state. The plurality of connectors are configured to engage a wall of a body lumen in the expanded state to inhibit migration of the endoprosthesis subsequent implanting the endoprosthesis in the body lumen.

8 Claims, 8 Drawing Sheets

(51) Int. Cl.
*A61F 2/89* (2013.01)
*A61F 2/88* (2006.01)
*A61F 2/915* (2013.01)
*A61F 2/848* (2013.01)

(52) U.S. Cl.
CPC .............. *A61F 2002/91516* (2013.01); *A61F 2002/91525* (2013.01); *A61F 2002/91566* (2013.01); *A61F 2230/0069* (2013.01); *A61F 2250/0039* (2013.01)

(58) Field of Classification Search
CPC .. A61F 2002/91558; A61F 2002/91575; A61F 2/89; A61F 2250/0039; A61F 2002/91541; A61F 2002/9511; A61F 2/88; A61F 2002/016; A61F 2002/91508; A61F 2230/009
See application file for complete search history.

(56) References Cited

U.S. PATENT DOCUMENTS

| | | |
|---|---|---|
| 5,674,277 A | 10/1997 | Freitag |
| 5,814,063 A | 9/1998 | Freitag |
| 6,210,429 B1 | 4/2001 | Vardi et al. |
| 7,527,644 B2 | 5/2009 | Mangiardi et al. |
| 7,547,321 B2 | 6/2009 | Silvestri et al. |
| 7,604,660 B2 | 10/2009 | Borg et al. |
| 7,608,099 B2 | 10/2009 | Johnson et al. |
| 7,637,934 B2 | 12/2009 | Mangiardi et al. |
| 7,637,942 B2 | 12/2009 | Mangiardi et al. |
| 7,651,520 B2 | 1/2010 | Fischell et al. |
| 7,731,654 B2 | 6/2010 | Mangiardi et al. |
| 7,785,360 B2 | 8/2010 | Freitag |
| 7,803,180 B2 | 9/2010 | Burpee et al. |
| 7,806,918 B2 | 10/2010 | Nissl et al. |
| 7,875,068 B2 | 1/2011 | Mangiardi et al. |
| 7,887,579 B2 | 2/2011 | Mangiardi et al. |
| 7,942,921 B2 | 5/2011 | Nissl et al. |
| 7,959,671 B2 | 6/2011 | Mangiardi et al. |
| 8,080,053 B2 | 12/2011 | Satasiya et al. |
| 8,128,679 B2 | 3/2012 | Casey |
| 8,142,488 B2 | 3/2012 | Reynolds et al. |
| 8,206,436 B2 | 6/2012 | Mangiardi et al. |
| 8,262,721 B2 | 9/2012 | Welborn et al. |
| 8,267,987 B2 | 9/2012 | Johnson et al. |
| 8,298,277 B2 | 10/2012 | Mangiardi et al. |
| 8,323,350 B2 | 12/2012 | Nissl |
| 8,353,946 B2 | 1/2013 | Mangiardi et al. |
| 8,535,366 B2 | 9/2013 | Mangiardi et al. |
| 8,535,370 B1* | 9/2013 | Eckert ................ A61F 2/07 623/1.13 |
| 8,652,196 B2 | 2/2014 | Nissl |
| 8,834,558 B2 | 9/2014 | Nissl |
| 8,926,683 B2 | 1/2015 | Gill et al. |
| 2005/0131515 A1 | 6/2005 | Cully et al. |
| 2007/0005127 A1 | 1/2007 | Boekstegers et al. |
| 2007/0213810 A1 | 9/2007 | Newhauser et al. |
| 2009/0187240 A1 | 7/2009 | Clerc et al. |
| 2009/0248132 A1 | 10/2009 | Bloom et al. |
| 2010/0286760 A1 | 11/2010 | Beach et al. |
| 2011/0093059 A1* | 4/2011 | Fischell .............. A61F 2/91 623/1.15 |
| 2011/0230957 A1 | 9/2011 | Bonsignore et al. |
| 2012/0150277 A1 | 6/2012 | Wood et al. |
| 2012/0310363 A1* | 12/2012 | Gill ..................... A61F 2/07 623/23.7 |
| 2013/0018215 A1 | 1/2013 | Snider et al. |
| 2013/0018452 A1 | 1/2013 | Weitzner et al. |
| 2013/0085565 A1 | 4/2013 | Eller et al. |
| 2013/0103163 A1 | 4/2013 | Krimsky et al. |
| 2013/0110253 A1 | 5/2013 | Gill et al. |
| 2013/0116770 A1 | 5/2013 | Robinson |
| 2013/0116771 A1 | 5/2013 | Robinson |
| 2013/0116772 A1 | 5/2013 | Robinson |
| 2013/0123897 A1 | 5/2013 | Robinson |
| 2013/0172983 A1 | 7/2013 | Clerc et al. |
| 2013/0184808 A1 | 7/2013 | Hall et al. |
| 2013/0184810 A1 | 7/2013 | Hall et al. |
| 2013/0325141 A1 | 12/2013 | Gill et al. |
| 2014/0067047 A1 | 3/2014 | Eller et al. |
| 2014/0079758 A1 | 3/2014 | Hall et al. |
| 2014/0081414 A1 | 3/2014 | Hall et al. |
| 2014/0086971 A1 | 3/2014 | Hall et al. |
| 2014/0248418 A1 | 9/2014 | Eller et al. |
| 2014/0249619 A1 | 9/2014 | Eller et al. |
| 2014/0257461 A1 | 9/2014 | Robinson et al. |
| 2014/0277562 A1 | 9/2014 | Seddon et al. |
| 2014/0277573 A1 | 9/2014 | Gill et al. |
| 2015/0073529 A1 | 3/2015 | Fleury et al. |
| 2015/0148887 A1 | 5/2015 | Beach et al. |

FOREIGN PATENT DOCUMENTS

| | | |
|---|---|---|
| WO | 2005053577 A2 | 6/2005 |
| WO | 2010124286 A1 | 10/2010 |
| WO | 2012047308 A1 | 4/2012 |
| WO | 2013074990 A1 | 5/2013 |
| WO | 2014159237 A1 | 10/2014 |

* cited by examiner

STENT WITH FLEXIBLE HINGE

CROSS REFERENCE TO RELATED APPLICATIONS

This application claims the benefit of U.S. Provisional Patent Application Ser. No. 62/067,039 filed on Oct. 22, 2014, the disclosure of which is incorporated herein by reference.

TECHNICAL FIELD

The disclosure is directed to an endoprosthesis, such as a stent, having anti-migration features and/or a flexible hinge feature. More particularly, the disclosure is directed to a covered stent having anti-migration features permitting tissue ingrowth through select portions of the stent and/or a flexible hinge feature which maintains luminal patency when bent.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. Bare or partially covered endoprostheses allow tissue ingrowth through the structure of the endoprosthesis to prevent migration of the endoprosthesis. However, if it is desired to remove the endoprosthesis at some later time, the ingrown tissue must be cut away, causing significant trauma to the body lumen. Fully covered stents, on the other hand, prevent tissue ingrowth to facilitate removal. However, fully covered endoprostheses are prone to migrate through the body lumen. Some patients require an endoprosthesis to be placed at a bend or bifurcation in the body lumen. However, some endoprostheses may be too stiff to maintain luminal patency around the bend or may not be long enough, requiring multiple endoprostheses (e.g., one stent placed before the bend and one stent placed after the bend, or overlapping stents at the bend).

Accordingly, it is desirable to provide endoprostheses that exhibit anti-migration features, while reducing the trauma to the body lumen of the patient if removal of the endoprosthesis is desired, and/or a flexible hinge feature for maintaining luminal patency around a bend in the body lumen.

SUMMARY

The disclosure is directed to several alternative designs, materials and methods of manufacturing medical device structures and assemblies, and uses thereof.

In a first aspect, an endoprosthesis may include an expandable tubular framework having a first end and a second end defining a length therebetween, and a lumen extending therethrough along a central longitudinal axis. The expandable tubular framework may be expandable from a compressed state to an expanded state and may include a plurality of strut rows, wherein adjacent strut rows define interstices therebetween, each interstice having a length along the central longitudinal axis and spacing the adjacent strut rows apart, and a plurality of connectors extending across the interstices between adjacent strut rows and interconnecting adjacent strut rows, at least some of the plurality of connectors defining a flexible hinge portion. The lengths of the interstices between adjacent strut rows may vary along the length of the expandable tubular framework. The plurality of connectors may extend radially outward beyond an outer diameter of the plurality of strut rows in the expanded state. The plurality of connectors may be configured to engage a wall of a body lumen in the expanded state to inhibit migration of the endoprosthesis subsequent implanting the endoprosthesis in the body lumen.

In addition or alternatively, the flexible hinge portion is bounded by two end portions of the expandable tubular framework, the two end portions having a greater stiffness than the flexible hinge portion.

In addition or alternatively, the flexible hinge portion is adapted to maintain at least 60% patency of the lumen when the expandable tubular framework is bent at the flexible hinge portion.

In addition or alternatively, the plurality of connectors each includes an angled segment arranged at a non-parallel angle relative to the central longitudinal axis.

In addition or alternatively, the plurality of strut rows of the expandable tubular framework includes a first strut row, a second strut row, a third strut row, and a fourth strut row. The plurality of connectors includes a first plurality of connectors interconnecting the first strut row and the second strut row, a second plurality of connectors interconnecting the second strut row and the third strut row, and a third plurality of connectors interconnecting the third strut row and the fourth strut row.

In addition or alternatively, the first plurality of connectors has a first connector length and the second plurality of connectors has a second connector length greater than the first connector length.

In addition or alternatively, the first plurality of connectors extends across a first interstice between the first strut row and the second strut row, the second plurality of connectors extends across a second interstice between the second strut row and the third strut row, and the third plurality of connectors extends across a third interstice between the third strut row and the fourth strut row. A length of the first interstice is different from a length of the second interstice.

In addition or alternatively, a length of the third interstice is different from the length of the second interstice.

In addition or alternatively, the plurality of strut rows of the expandable tubular framework includes a fifth strut row. The plurality of connectors includes a fourth plurality of connectors extending across a fourth interstice between the fourth strut row and the fifth strut row and interconnecting the fourth strut row and the fifth strut row. The length of the first interstice is less than the length of the second interstice, the length of the second interstice and a length of the third interstice are approximately equal, and a length of the fourth interstice is less than the length of the third interstice.

In addition or alternatively, the first plurality of connectors each includes an angled segment arranged at a different angle relative to the central longitudinal axis than the second plurality of connectors.

In addition or alternatively, the first plurality of connectors extends in a first helical direction and the second plurality of connectors extends in a second helical direction, opposite the first helical direction. The third plurality of connectors extends in the first helical direction.

In addition or alternatively, an endoprosthesis may include a polymeric cover covering the plurality of strut rows and spanning the interstices between adjacent strut rows.

In addition or alternatively, spaces between the plurality of connectors and the plurality of strut rows to which the plurality of connectors is interconnected with is devoid of the polymeric cover to permit tissue ingrowth around the plurality of connectors.

In addition or alternatively, an endoprosthesis may include a second expandable tubular framework configured to be positioned through a side of the expandable tubular framework within an enlarged opening in the flexible hinge portion. When the second expandable tubular framework is positioned through the side of the expandable tubular framework, a first end portion of the second expandable tubular framework is positioned within the lumen of the expandable tubular framework and an opposing second end portion is positioned outside of the expandable tubular framework.

In addition or alternatively, the first end portion of the second expandable tubular framework includes a circumferential ridge portion configured to engage the expandable tubular framework, the circumferential ridge portion having a greater maximum outer extent than the enlarged opening.

In addition or alternatively, an endoprosthesis may include an expandable tubular framework having a first end and a second end defining a length therebetween, and a lumen extending therethrough along a central longitudinal axis. The expandable tubular framework may be expandable from a compressed state to an expanded state and may include a plurality of strut rows including at least a first strut row, a second strut row, a third strut row, and a fourth strut row. The expandable tubular framework may include a first plurality of connectors extending across a first gap between the first strut row and the second strut row and interconnecting the first strut row and the second strut row, the first gap having a first length, a second plurality of connectors extending across a second gap between the third strut row and the fourth strut row and interconnecting the third strut row and the fourth strut row, the second gap having a second length, and a third plurality of connectors extending across a third gap and interconnecting adjacent strut rows intermediate the first plurality of connectors and the second plurality of connectors, the third gap having a third length. The plurality of strut rows may define an outer diameter in the expanded state. At least one of the first plurality of connectors, the second plurality of connectors, and the third plurality of connectors may extend radially outward beyond the outer diameter in the expanded state. The third length may be greater than the first length and the second length.

In addition or alternatively, the third plurality of connectors interconnect the second strut row and the third strut row.

In addition or alternatively, the first plurality of connectors extends in a first helical direction, the third plurality of connectors extends in a second helical direction opposite the first helical direction, and the second plurality of connectors extends in the first helical direction.

In addition or alternatively, an endoprosthesis may include a fourth plurality of connectors extending across a fourth gap and interconnecting adjacent strut rows intermediate the first plurality of connectors and the second plurality of connectors, the fourth gap having a fourth length. The fourth length is greater than the first length and the second length.

In addition or alternatively, an endoprosthesis may include a polymeric cover covering the plurality of strut rows and spanning the first, second, and third gaps. Spaces between the first plurality of connectors and the first strut row and the second strut row are devoid of the polymeric cover and open to permit tissue ingrowth therethrough. Spaces between the second plurality of connectors and the third strut row and the fourth strut row are devoid of the polymeric cover and open to permit tissue ingrowth therethrough. Spaces between the third plurality of connectors and the adjacent strut rows interconnected thereto are devoid of the polymeric cover and open to permit tissue ingrowth therethrough.

In addition or alternatively, an endoprosthesis may include an expandable tubular framework having a first end and a second end defining a length therebetween, and a lumen extending therethrough along a central longitudinal axis. The expandable tubular framework may be expandable from a compressed state to an expanded state and may include a plurality of strut rows including at least a first strut row, a second strut row, a third strut row, and a fourth strut row. Each strut row may include alternating peaks and valleys. The expandable tubular framework may include a first plurality of connectors extending across a first gap between peaks of the first strut row and peaks of the second strut row and interconnecting the first strut row and the second strut row, the first gap having a first length, a second plurality of connectors extending across a second gap between peaks of the third strut row and peaks of the fourth strut row and interconnecting the third strut row and the fourth strut row, the second gap having a second length, and a third plurality of connectors extending across a third gap and interconnecting peaks of adjacent strut rows intermediate the first plurality of connectors and the second plurality of connectors, the third gap having a third length. The third length may be greater than the first length and the second length such that the third plurality of connectors define a flexible hinge portion.

In addition or alternatively, the flexible hinge portion may be between first and second end portions of the expandable tubular framework. The first end portion may include the first and second strut rows and the first plurality of connectors therebetween. The second end portion may include the third and fourth strut rows and the second plurality of connectors therebetween.

In addition or alternatively, an endoprosthesis may include a polymeric cover covering the plurality of strut rows and spanning the first, second, and third gaps. Spaces between the first plurality of connectors and the first strut row and the second strut row are devoid of the polymeric cover and open to permit tissue ingrowth therethrough. Spaces between the second plurality of connectors and the third strut row and the fourth strut row are devoid of the polymeric cover and open to permit tissue ingrowth therethrough. Spaces between the third plurality of connectors and the adjacent strut rows interconnected thereto are devoid of the polymeric cover and open to permit tissue ingrowth therethrough.

The above summary of some embodiments, aspects, and/or examples is not intended to describe each disclosed embodiment or every implementation of the present disclosure. The Figures, and Detailed Description, which follow, more particularly exemplify these embodiments.

BRIEF DESCRIPTION OF THE DRAWINGS

The aspects of the disclosure may be more completely understood in consideration of the following detailed description of various embodiments in connection with the accompanying drawings, in which.

Figure 1:
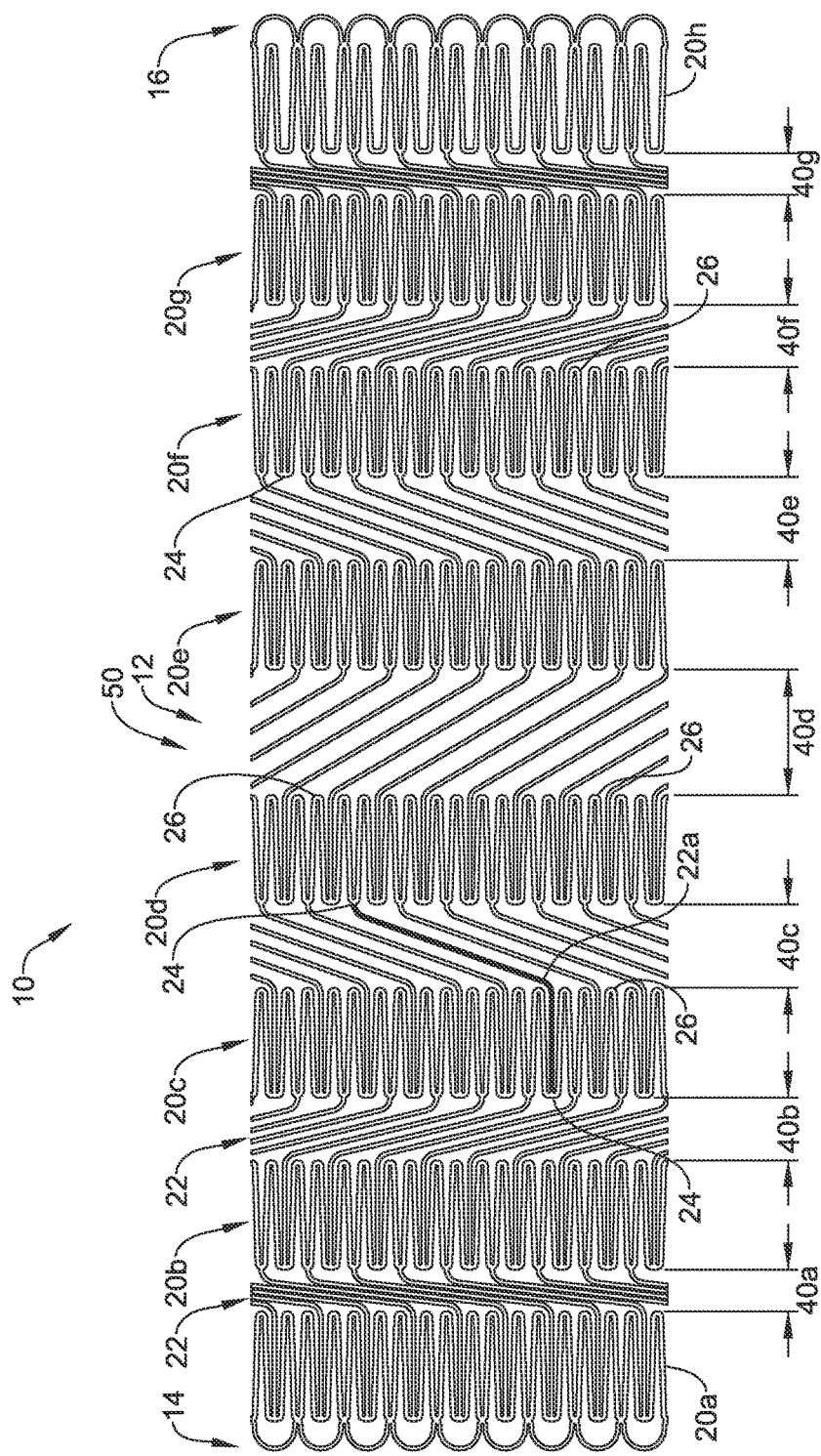
FIG. 1 is a schematic view of an expandable tubular framework of an example endoprosthesis in a compressed state as if the expandable tubular framework were cut longitudinally and flattened.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

An exemplary implantable endoprosthesis 10 may be configured to be positioned in a body lumen for a variety of medical applications. For example, the endoprosthesis 10 may be used to treat a stenosis in a blood vessel, used to maintain a fluid opening or pathway in the vascular, urinary, biliary, tracheobronchial, esophageal, or renal tracts, or position a device such as an artificial valve or filter within a body lumen, in some instances. In some instances, the endoprosthesis 10 may be a prosthetic graft, a stent-graft, or a stent (e.g., a vascular stent, tracheal stent, bronchial stent, esophageal stent, etc.). Although illustrated herein as a stent, the endoprosthesis 10 may be any of a number of devices that may be introduced endoscopically, subcutaneously, percutaneously, or surgically to be positioned within an organ, tissue, or lumen, such as a heart, artery, vein, urethra, esophagus, trachea, bronchus, bile duct, or the like.

In some instances, the endoprosthesis 10 may be a self-expanding endoprosthesis configured to automatically expand from a compressed state to an expanded state upon the removal of a constraining force acting on the endoprosthesis. In other instances, the endoprosthesis 10 may be a mechanically expandable endoprosthesis configured to be expanded from a compressed state to an expanded state through the application of a mechanical force acting on the endoprosthesis 10 (e.g., a radially expanding balloon).

The endoprosthesis 10 may be a generally tubular member having an expandable tubular framework 12 having a first end 14 and a second end 16 defining a length therebetween, a lumen 18 extending therethrough along a central longitudinal axis, an outer diameter defining an outer surface, and an inner diameter defining an inner surface forming the lumen 18 extending therethrough. The expandable tubular framework 12 may include a plurality of strut rows 20 arranged along the length of the endoprosthesis 10. In some instances, the strut rows 20 may extend circumferentially around a perimeter of the expandable tubular framework 12.

As used herein, the outer surface of the expandable tubular framework 12 is intended to refer to a radially outward facing surface of the plurality of strut rows 20 commensurate with the outer diameter of the endoprosthesis 10. As used herein, the inner surface is intended to refer to a radially inward facing surface of the plurality of strut rows 20 commensurate with the inner diameter of the endoprosthesis 10.

The expandable tubular framework 12 may include a plurality of strut rows 20 and a plurality of connectors 22 interconnecting adjacent strut rows 20. For example, the plurality of strut rows 20 may include two, three, four, five, six, seven, eight, nine, ten or more strut rows arranged along the length of the expandable tubular framework 12. In some instances, the plurality of connectors 22 may include a first plurality of connectors, a second plurality of connectors, a third plurality of connectors, a fourth plurality of connectors, a fifth plurality of connectors, a sixth plurality of connectors, a seventh plurality of connectors, an eighth plurality of connectors, a ninth plurality of connectors, a tenth plurality of connectors, or more arranged along the length of the expandable tubular framework 12. Adjacent strut rows may define a gap or interstice 40 therebetween, each gap or interstice 40 having a length measured along the central longitudinal axis and spacing the adjacent strut rows 20 apart by the gap or interstice 40. The plurality of connectors 22 may extend across the gaps or interstices 40 between adjacent strut rows 20. Thus, the length of the endoprosthesis 10 may be dictated, at least in part, by the number of strut rows 20 and/or the length(s) of the gaps or interstices 40.

Each strut row 20 may include continuously undulating struts defining interstitial spaces or openings therebetween. The undulating struts of each strut row 20 may include alternating peaks 24 and valleys 26, the peaks 24 and valleys 26 corresponding to where individual segments of the undulating struts converge and/or diverge forming strut pairs. The peaks 24 associated with a strut row 20 are located toward the first end 14 of the expandable tubular framework 12 while the valleys 26 associated with a strut row 20 are located toward the second end 16 of the expandable tubular framework 12.

The endoprosthesis 10 may be formed of any desired material, such as a biocompatible material including biostable, bioabsorbable, biodegradable or bioerodible materials. For instance, the endoprosthesis 10 may be formed of a metallic material, a polymeric material, or suitable combinations thereof. Some suitable metallic materials include, but are not necessarily limited to, stainless steel, tantalum, tungsten, nickel-titanium alloys such as those possessing shape memory properties commonly referred to as nitinol, nickel-chromium alloys, nickel-chromium-iron alloys, cobalt-chromium-nickel alloys, or other suitable metals, or combinations or alloys thereof. Some suitable polymeric materials include, but are not necessarily limited to, polyamide, polyether block amide, polyethylene, polyethylene terephthalate, polypropylene, polyvinylchloride, polyurethane, polytetrafluoroethylene, polysulfone, and copolymers, blends, mixtures or combinations thereof.

Figure 4:
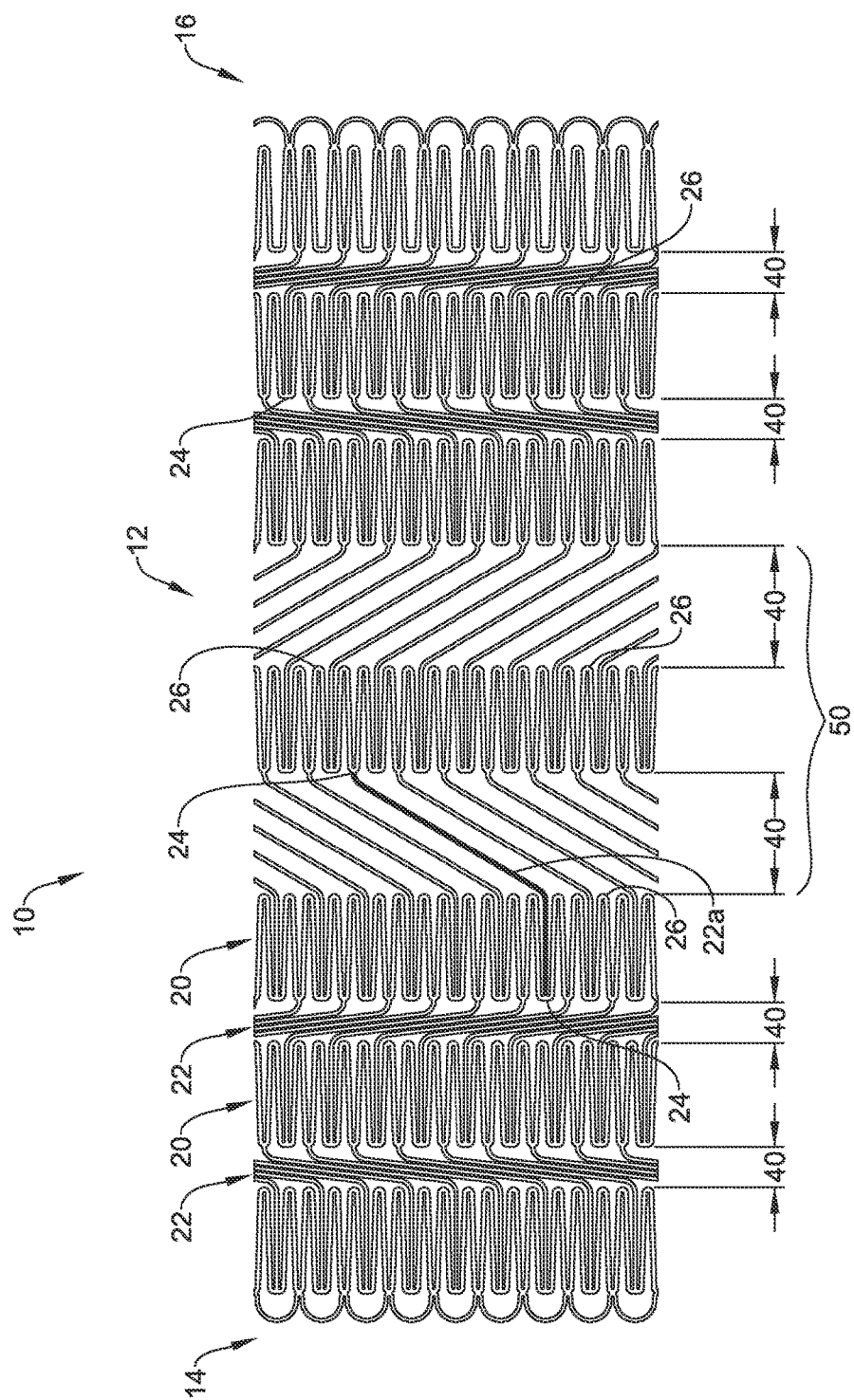
FIG. 4 is a schematic view of an expandable tubular framework of an example endoprosthesis in a compressed state as if the expandable tubular framework were cut longitudinally and flattened.

In some instances, the expandable tubular framework 12 of the endoprosthesis 10 may be formed as a monolithic structure from a single tubular member, such as a metallic tube. For example, the expandable tubular framework 12 may be cut (e.g., laser cut) from a single metallic tubular member and then expanded. Thus, the plurality of strut rows 20 and the plurality of connectors 22 of the expandable tubular framework 12 may be formed as a monolithic structure cut from a single metallic tube, in some instances. In some instances, the plurality of strut rows 20 and the plurality of connectors 22 of the expandable tubular framework 12 may be cut from a single polymeric tubular member. In some embodiments, the expandable tubular framework 12 may be machined, chemically etched, or otherwise formed as a monolithic structure from a single tubular member. FIGS. 1 and 4 illustrate a schematic view of two possible exemplary patterns cut into the metallic tubular member to form the expandable tubular framework 12 of the endoprosthesis 10. It is noted that the pattern shown in FIGS. 1 and 4 is illustrated as if the expandable tubular framework 12 were cut longitudinally and flattened, but one of skill in the art would understand that the pattern would extend circumferentially around the metallic tube. As shown in FIGS. 1 and 4, in the compressed state, the peaks 24 and valleys 26 of the plurality of strut rows 20 are closely arranged, and the plurality of connectors 22 are arranged in a parallel arrangement with respect to each other, with the plurality of connectors 22 arranged at a non-parallel angle (e.g., an acute angle) relative to the longitudinal axis of the expandable tubular framework 12 between adjacent strut rows 20.

Each of the plurality of connectors 22 may have a first end 36 connected to a peak 24 in a strut row 20 (e.g., a first strut row, a second strut row, etc.) and a second end 38 connected to a peak 24 in an adjacent strut row 20 (e.g., a second strut row, a third strut row, etc.). Thus, each connector 22 may extend from a peak 24 in a first strut row 20 to a peak 24 in a second strut row 20, from a peak 24 in a second strut row 20 to a peak 24 in a third strut row 20, from a peak 24 in a third strut row 20 to a peak 24 in a fourth strut row, etc. As an example, a first plurality of connectors 22 may extend from a first strut row 20 to a second strut row 20, a second plurality of connectors 22 may extend from the second strut row 20 to a third strut row 20, a third plurality of connectors 22 may extend from the third strut row 20 to a fourth strut row 20, a fourth plurality of connectors 22 may extend from the fourth strut row 20 to a fifth strut row 20, a fifth plurality of connectors 22 may extend from the fifth strut row 20 to a sixth strut row 20, a sixth plurality of connectors 22 may extend from the sixth strut row 20 to a seventh strut row 20, a seventh plurality of connectors 22 may extend from the seventh strut row 20 to an eighth strut row 20, an eighth plurality of connectors 22 may extend from the eighth strut row 20 to a ninth strut row 20, a ninth plurality of connectors 22 may extend from the ninth strut row 20 to a tenth strut row 20, etc.

In some instances, a first plurality of connectors 22 may extend in a first helical direction (e.g., counterclockwise as viewed along the central longitudinal axis of the endoprosthesis 10 toward the second end 16 from the first end 14) from the first strut row 20 to the second strut row 20. A second plurality of connectors 22 may extend in a second helical direction (e.g., clockwise as viewed along the central longitudinal axis of the endoprosthesis 10 toward the second end 16 from the first end 14), opposite the first helical direction, from the second strut row 20 to the third strut row 20. A third plurality of connectors 22 may extend in the first helical direction (e.g., counterclockwise as viewed along the central longitudinal axis of the endoprosthesis 10 toward the second end 16 from the first end 14) from the third strut row 20 to the fourth strut row 20. A fourth plurality of connectors 22 may extend in the second helical direction (e.g., clockwise as viewed along the central longitudinal axis of the endoprosthesis 10 toward the second end 16 from the first end 14), opposite the first helical direction, from the fourth strut row 20 to the fifth strut row 20. In other words, the plurality of connectors 22 may alternate helical directions between adjacent strut rows 20 along the length of the expandable tubular framework 12 and/or the endoprosthesis 10. Such an arrangement of the plurality of connectors 22 may assist in resisting or cancelling twisting or torsional forces imparted on the endoprosthesis 10.

For example, in some instances, the alternating direction of the helical arrangement of the plurality of connectors 22 between adjacent strut rows 20 may reduce and/or eliminate twisting of the expandable tubular framework 12 as the expandable tubular framework 12 expands from the compressed state to the expanded state. In other words, any twisting between the first strut row 20 and the second strut row 20 in a first direction (e.g., clockwise or counterclockwise) may be offset by counter-twisting between the second strut row 20 and the third strut row 20 in an opposite second direction (e.g., counterclockwise or clockwise), for example.

Figure 2:
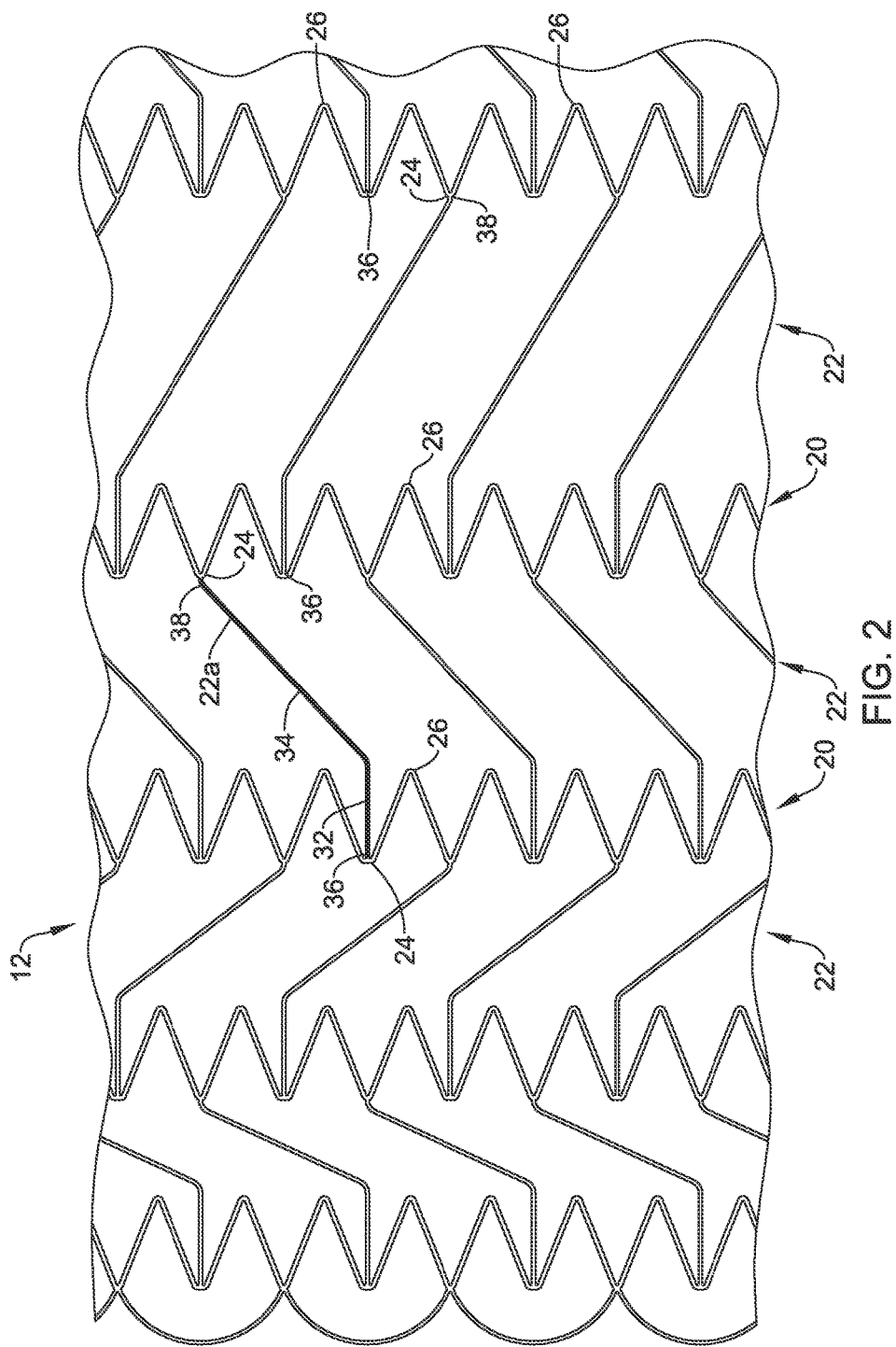
FIG. 2 is a schematic view of a portion of the expandable tubular framework of FIG. 1 in an expanded state.

A first connector 22a of a plurality of connectors 22 is shaded in FIGS. 1 and 2 for illustration purposes. For the purpose of illustration, the plurality of connectors 22 having the first connector 22a may be designated a first plurality of connectors 22. All, some, or none of the plurality of connectors 22 may be arranged, configured, and/or constructed as described in conjunction with the first connector 22a, as desired. The first connector 22a may extend from a peak 24 of a first strut row 20 to a peak 24 of an adjacent second strut row 20 in a helical fashion, with the first end 36 of the first connector 22a connected to the first strut row 20 being circumferentially offset from the second end 38 of the first connector 22a connected to the second strut row 20. Each of the plurality of connectors 22 may be similarly arranged. In the compressed state after cutting the pattern in the metallic tube, the plurality of connectors 22 may be positioned at the same radial distance as the plurality of strut rows 20 from the central longitudinal axis of the expandable tubular framework 12. In other words, in the compressed state, the endoprosthesis 10 may have a generally uniform and/or constant outer diameter or maximum outer extent.

A second connector of a second plurality of connectors 22 extending between the second strut row 20 and an adjacent third strut row 20 may have a first end 36 connected to a peak 24 of the second strut row 20 and a second end 38 connected to a peak 24 of the third strut row 20, with the first end 36 of the second connector and the second end 38 of the second connector being circumferentially offset from each other. The first end 36 of the second connector may be circumferentially located between the first end 36 and the second end 38 of the first connector 22a. A third connector of the third plurality of connectors 22 extending between the third strut row 20 and an adjacent fourth strut row 20 may have a first end 36 connected to a peak 24 of the third strut row 20 and a second end 38 connected to a peak 24 of the fourth strut row 20, with the first end 36 of the third connector and the second end 38 of the third connector being circumferentially offset from each other. The first end 36 of the third connector may be circumferentially located between the first end 36 and the second end 38 of the second connector. In some embodiments, each of the plurality of connectors 22 may circumferentially skip over a peak 24 between the first end 36 and the second end 38. In other words, each of the plurality of connectors 22 may have a first end 36 connected to a first peak 24 and a second end 38 connected to a third peak 24 circumferentially offset from the first peak 24 by at least one intervening (e.g., second) peak 24. The plurality of connectors 22 may be similarly arranged.

Figure 5:
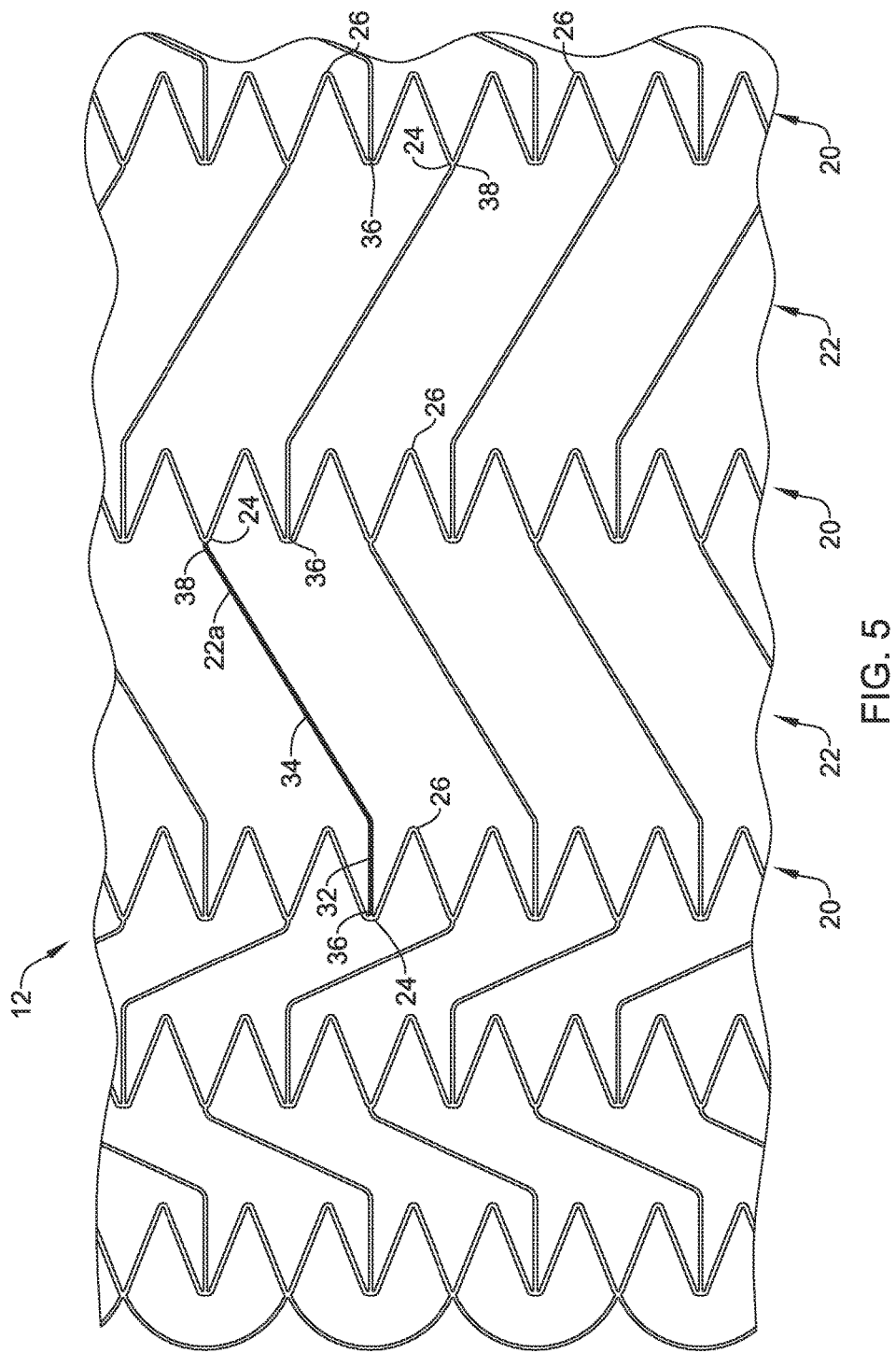
FIG. 5 is a schematic view of a portion of the expandable tubular framework of FIG. 4 in an expanded state.

Once the pattern has been cut into the metallic tube, the expandable tubular framework 12 may be expanded from the compressed state in which it was cut from the metallic tube to an expanded state. For example, a radially outward force may be applied to the inner surface of the expandable tubular framework 12 to expand the plurality of strut rows 20 from a first diameter in the compressed state to a second, enlarged diameter (e.g., an outer diameter defining an outer surface) in the expanded state, causing the peaks 24 and valleys 26 of the plurality of strut rows 20 to move farther apart circumferentially. FIGS. 2 and 5 illustrate an enlarged view of a portion of the pattern of the expandable tubular framework 12 in the expanded state. Furthermore, in some embodiments, a non-parallel angle (e.g., an acute angle) of the plurality of connectors 22 relative to the central longitudinal axis of the expandable tubular framework 12 in the expanded state may be less than a non-parallel angle (e.g., an acute angle) of the plurality of connectors 22 relative to the central longitudinal axis of the expandable tubular framework 12 in the compressed state.

As shown in FIGS. 2 and 5, the plurality of connectors 22 may each include a first end 36 connected to a strut row 20 (e.g., a first strut row 20) and a second end 38 connected to an adjacent strut row (e.g., a second strut row 20). In at least some instances, the plurality of connectors 22 may each include a longitudinal segment 32 extending distally toward the second end 16 from a peak 24 of the strut row 20 (e.g. the first strut row 20) and an angled segment 34 extending proximally toward the first end 14 from a peak 24 of the adjacent strut row 20 (e.g., the second strut row 20). The peaks 24 of adjacent strut rows 20 may be generally aligned with each other parallel to the central longitudinal axis of the expandable tubular framework 12. The longitudinal segment 32 may extend generally parallel to the central longitudinal axis of the expandable tubular framework 12, while the angled segment 34 may extend and/or be arranged at a non-parallel angle (e.g., an acute angle) relative to the central longitudinal axis of the expandable tubular framework 12. In some embodiments, the first plurality of connectors 22 may each include an angled segment 34 arranged at a different angle relative to the central longitudinal axis than the second plurality of connectors 22. In some embodiments, the second plurality of connectors 22 may each include an angled segment 34 arranged at a different angle relative to the central longitudinal axis of the expandable tubular framework 12 than the third plurality of connectors 22, etc. In other words, each identified subset (e.g., first plurality of connectors, second plurality of connectors, third plurality of connectors, etc.) or "grouped" plurality of connectors 22 may each include an angled segment 34 arranged at a different angle relative to the central longitudinal axis of the expandable tubular framework 12 than a different plurality of connectors 22.

In some embodiments, an angled segment 34 may "skip over" one intervening peak 24 of the adjacent strut row 20 (e.g., the second strut row 20) before connecting at its second end 38 to a peak 24 of the adjacent strut row 20 (e.g., the second strut row 20). In some embodiments, an angled segment 34 may "skip over" more than one intervening peak 24 of the adjacent strut row 20 (e.g., the second strut row 20) before connecting at its second end 38 to a peak 24 of the adjacent strut row 20 (e.g., the second strut row 20). The plurality of connectors 22 between and/or connecting the plurality of strut rows 20 may be similarly arranged.

As the expandable tubular framework 12 is radially expanded from the compressed state to the expanded state, the plurality of connectors 22 may extend radially outward beyond the outer surface and/or the outer diameter of the plurality of strut rows 20, such as along a curvilinear or arcuate pathway between adjacent strut rows 20 to which the ends of the plurality of connectors 22 are connected to. Accordingly, in the expanded state, the plurality of connectors 22 may extend further from the central longitudinal axis of the expandable tubular framework 12 than the plurality of strut rows 20 such that the plurality of connectors 22 extend above and/or radially outward of the plurality of strut rows 20.

Figure 3:
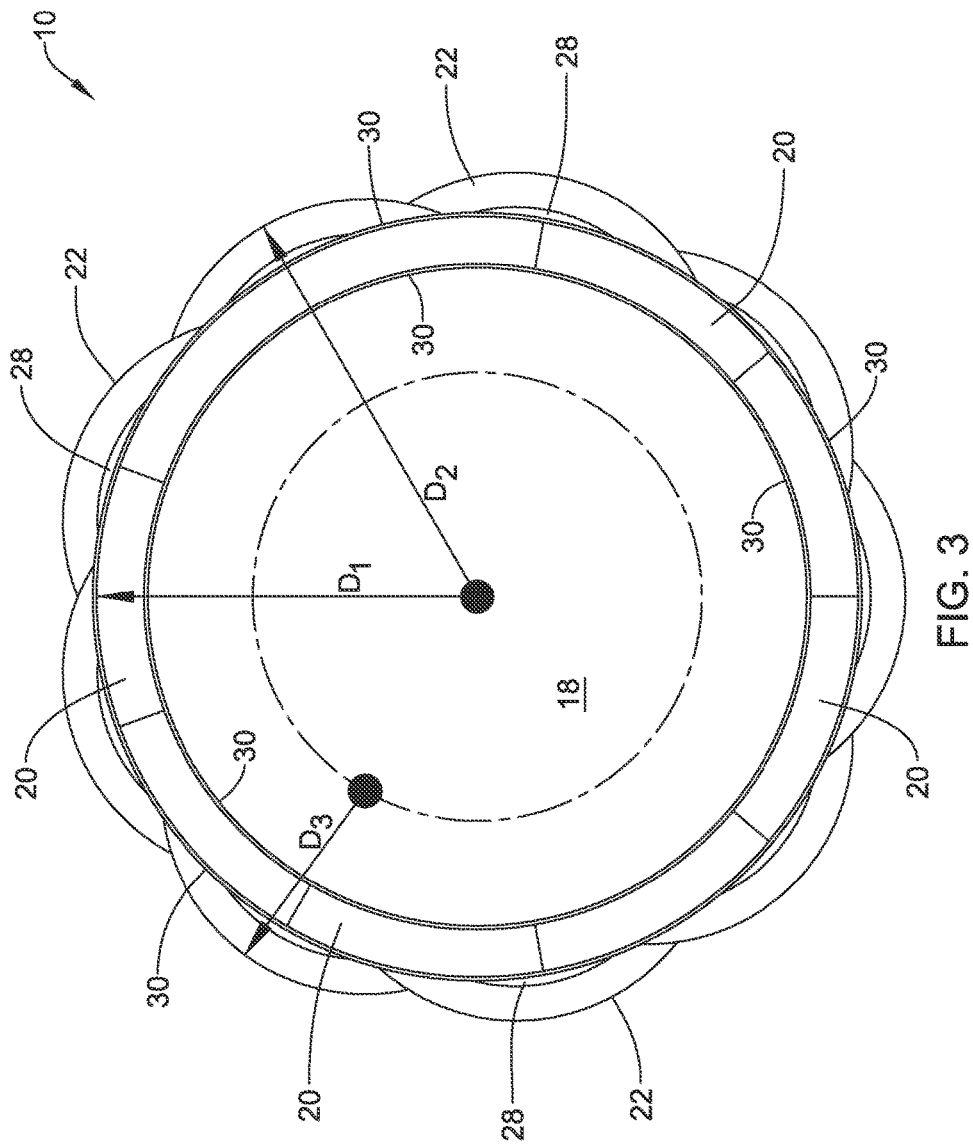
FIG. 3 is an end view of an example endoprosthesis in an expanded state.

As seen in FIG. 3, when an endoprosthesis 10 is in the expanded state, the plurality of strut rows 20 may extend a first distance D1 radially outward from the central longitudinal axis of the expandable tubular framework 12 to an outer diameter defining an outer surface of the expandable tubular framework 12. In some instances, the first distance D1 may define a radius and/or a maximum outer extent of the plurality of strut rows 20 and/or the outer surface of the expandable tubular framework 12. When in the expanded state, each of the plurality of connectors 22 may extend along a curved or arcuate pathway between adjacent strut rows 20 to a second distance D2 radially outward from the central longitudinal axis beyond the outer diameter of the plurality of strut rows 20 of the expandable tubular framework 12. For example, a maximum outer extent of the plurality of connectors 22 may extend to a second distance D2 from the central longitudinal axis of the expandable tubular framework 12, wherein the second distance D2 is greater than the first distance D1. In some instances, a curvature of the plurality of connectors 22 at the maximum outer extent of the plurality of connectors 22 may be defined by/as a third distance D3 corresponding to a radius of the plurality of connectors 22. In some instances, the third distance D3 and/or the radius of the plurality of connectors 22 is less than the first distance D1 and/or the radius of the plurality of strut rows 20. In other words, for each of the plurality of connectors 22, the third distance D3 may be defined along (or measured from) a longitudinal axis radially offset from and parallel to the central longitudinal axis of the expandable tubular framework 12. The offset longitudinal axes defining the third distance D3 for each of the plurality of connectors 22, if viewed collectively from an end of the endoprosthesis 10 as in FIG. 3, may define points along a generally circular path about the central longitudinal axis of the expandable tubular framework 12.

The plurality of connectors 22 may be configured to engage a wall of a body lumen in the expanded state to inhibit migration of the endoprosthesis 10 subsequent to implanting the endoprosthesis 10 in the body lumen. For example, the plurality of connectors 22 may engage the tissue between cartilage rings within the tracheal anatomy to provide anti-migration support for the endoprosthesis 10.

In the expanded state, a space or opening 28 may be defined between each of the curved or arcuate plurality of connectors 22 and the outer diameter of the plurality of strut rows 20 as viewed along the central longitudinal axis of the expandable tubular framework 12 from the end of the endoprosthesis 10, as shown in FIG. 3. In some instances, the space or opening 28 may be unobstructed by any other structure of the endoprosthesis 10. In some instances, the space or opening 28 may be configured to accept tissue ingrowth and/or the plurality of connectors 22 may be configured to engage tissue or be encapsulated by tissue ingrowth. Accordingly, tissue ingrowth through the space or opening 28 and covering or encapsulating the plurality of connectors 22 subsequent to implanting the endoprosthesis 10 may further secure the endoprosthesis 10 in place within the patient's anatomy and thereby prevent migration of the endoprosthesis 10.

As described above, each gap or interstice 40 between adjacent strut rows 20 may have a length along the central longitudinal axis of the expandable tubular framework 12 and may space the adjacent strut rows 20 apart. In at least some embodiments, the gaps or interstices 40 between adjacent strut rows 20 may be defined between the valley(s) 26 of one strut row 20 and the peak(s) 24 of another strut row 20 immediately adjacent to the valley(s) 26. In some embodiments, the lengths of the gaps or interstices 40 between adjacent strut rows 20 may vary along the length of the expandable tubular framework 12. For example, the length of the gap or interstice 40 between adjacent strut rows 20 in a first end region and/or a second end region of the expandable framework 12 may be less than the length of the gap or interstice 40 between adjacent strut rows 20 in a central portion of the expandable framework 12 between the first and second end regions.

As an example, in some embodiments, a first strut row 20 and a second strut row 20 may define a first gap or interstice 40 therebetween, the second strut row 20 and a third strut row 20 may define a second gap or interstice 40 therebetween, and the third strut row 20 and a fourth strut row 20 may define a third gap or interstice 40 therebetween, wherein a length of the first interstice 40 may be different from a length of the second interstice 40 and/or a length of the third interstice 40 may be different from the length of the second interstice 40. In one instance, a first interstice, a second interstice, and a third interstice may each be different lengths. In another instance, a first interstice may be shorter than a second interstice, which may be shorter than a third interstice. In yet another instance, a first interstice and a third interstice may be a same length that is a different length (e.g., shorter or longer) than a second interstice. Taking into account that numerical nomenclature may be changed to accommodate different arrangements, each of the above-described instances may be seen illustrated in FIGS. 1-2.

In some embodiments, an endoprosthesis 10 may include an expandable tubular framework 12 having a first end 14 and a second end 16 defining a length therebetween, and a lumen 18 extending therethrough along a central longitudinal axis, the expandable tubular framework 12 being expandable from a compressed state to an expanded state. In some instances, the expandable tubular framework 12 may include a plurality of strut rows 20 including at least a first strut row, a second strut row, a third strut row, and a fourth strut row.

In some instances, the expandable tubular framework 12 may include a first plurality of connectors extending across a first gap or interstice between the first strut row and the second strut row and interconnecting the first strut row and the second strut row, the first gap or interstice having a first length. In some instances, the expandable tubular framework 12 may include a second plurality of connectors extending across a second gap or interstice between the third strut row and the fourth strut row and interconnecting the third strut row and the fourth strut row, the second gap or interstice having a second length. In some instances, the expandable tubular framework 12 may include a third plurality of connectors extending across a third gap or interstice and interconnecting adjacent strut rows intermediate the first plurality of connectors and the second plurality of connectors, the third gap or interstice having a third length. In other words, the third plurality of connectors may be disposed between the first plurality of connectors and the second plurality of connectors along the central longitudinal axis of the expandable tubular framework 12. In some embodiments, the third plurality of connectors may interconnect the second strut row and the third strut row. In some embodiments, the third plurality of connectors may be spaced apart from the second strut row and/or the third strut row. In at least some embodiments, at least one of the first plurality of connectors, the second plurality of connectors, and the third plurality of connectors extends radially outward beyond the outer diameter in the expanded state. In some instances, the third length may be greater than the first length and the second length, such that the expandable tubular framework 12 includes a flexible hinge portion. In some embodiments, an endoprosthesis 10 may include a fourth plurality of connectors extending across a fourth gap and interconnecting adjacent strut rows intermediate the first plurality of connectors and the second plurality of connectors, the fourth gap having a fourth length. In some instances, the fourth length is greater than the first length and the second length. In other words, the fourth plurality of connectors may be disposed between the first plurality of connectors and the second plurality of connectors along the central longitudinal axis of the expandable tubular framework 12.

In the embodiment of FIG. 1, the expandable framework 12 may include a first strut row 20a, a second strut row 20b, a third strut row 20c, a fourth strut row 20d, a fifth strut row 20e, a sixth strut row 20f, a seventh strut row 20g, and an eighth strut row 20h. The expandable framework 12 may include a first plurality of connectors 22 extending across a first gap or interstice 40a between the first strut row 20a and the second strut row 20b, a second plurality of connectors 22 extending across a second gap or interstice 40b between the second strut row 20b and the third strut row 20c, a third plurality of connectors 22 extending across a third gap or interstice 40c between the third strut row 20c and the fourth strut row 20d, a fourth plurality of connectors 22 extending across a fourth gap or interstice 40d between the fourth strut row 20d and the fifth strut row 20e, a fifth plurality of connectors 22 extending across a fifth gap or interstice 40e between the fifth strut row 20e and the sixth strut row 20f, a sixth plurality of connectors 22 extending across a sixth gap or interstice 40f between the sixth strut row 20f and the seventh strut row 20g, and a seventh plurality of connectors 22 extending across a seventh gap or interstice 40g between the seventh strut row 20g and the eighth strut row 20h.

The length of the gap or interstice 40 between adjacent strut rows 20 for one or more of the intermediate plurality of connectors 22 may be greater than for the length of the gap or interstice 40 between an adjacent plurality of connectors 22. For example, the length of the second gap 40b and/or the sixth gap 40f may be greater than the length of the first gap 40a and/or the seventh gap 40g, the length of the third gap 40c and/or the fifth gap 40e may be greater than the length of the first gap 40a, second gap 40b, sixth gap 40f and/or seventh gap 40g, and/or the length of the fourth gap 40d may be greater than the length of the first gap 40a, second gap 40b, third gap 40c, fifth gap 40e, sixth gap 40f and/or seventh gap 40g.

At least some of the plurality of connectors 22 may define a flexible hinge portion 50 having a greater lateral flexibility than other portions of the expandable framework 12. For example, one or more of the intermediate plurality of connectors 22 (which may extend across a gap or interstice 40 having a length greater than an adjacent gap or interstice 40) may provide a flexible hinge portion 50. The flexible hinge portion 50 may be bounded by two opposing end portions of the expandable tubular framework 12 made up of one or more strut rows 20 and associated connectors 22. In at least some embodiments, the two end portions may have a greater stiffness than the flexible hinge portion 50.

In some embodiments, an endoprosthesis 10 may include a polymeric cover 30 covering the plurality of strut rows and spanning the first, second, and third gaps or interstices. In some embodiments, openings or spaces 28 between the first plurality of connectors and the first strut row and the second strut row are devoid of the polymeric cover 30 and open to permit tissue ingrowth therethrough. In some embodiments, openings or spaces 28 between the second plurality of connectors and the third strut row and the fourth strut row are devoid of the polymeric cover 30 and open to permit tissue ingrowth therethrough. In some embodiments, openings or spaces 28 between the third plurality of connectors and the adjacent strut rows interconnected thereto are devoid of the polymeric cover 30 and open to permit tissue ingrowth therethrough. In some embodiments, openings or spaces 28 between the fourth plurality of connectors and the adjacent strut rows interconnected thereto are devoid of the polymeric cover 30 and open to permit tissue ingrowth therethrough.

In another example, illustrated in FIGS. 4-5, the plurality of strut rows 20 may include a fifth strut row 20, wherein the fourth strut row 20 and the fifth strut row 20 may define a fourth gap or interstice 40 therebetween, wherein the length of the first interstice is less than the length of the second interstice. In some instances, the length of the first interstice may be less than the length of the third interstice. In some instances, the length of the second interstice and the length of the third interstice may be approximately equal. In some instances, the length of the fourth interstice may be less than the length of the second interstice. In some instances, the length of the fourth interstice may be less than the length of the third interstice. In some instances, the length of the first interstice and the length of the fourth interstice may be approximately equal. In some instances, the length of the first interstice and the length of the fourth interstice may be different. In some instances, the length of the first interstice and the length of the fourth interstice may be less than the length of the second interstice and the length of the third interstice. Other arrangements are also contemplated.

In the embodiment of FIG. 4, the expandable framework 12 may include a first strut row 20, a second strut row 20, a third strut row 20, a fourth strut row 20, a fifth strut row 20, a sixth strut row 20, and a seventh strut row 20g. The expandable framework 12 may include a first plurality of connectors 22 extending across a first gap or interstice 40 between the first strut row 20 and the second strut row 20, a second plurality of connectors 22 extending across a second gap or interstice between the second strut row 20 and the third strut row 20, a third plurality of connectors 22 extending across a third gap or interstice 40 between the third strut row 20 and the fourth strut row 20, a fourth plurality of connectors 22 extending across a fourth gap or interstice 40 between the fourth strut row 20 and the fifth strut row 20, a fifth plurality of connectors 22 extending across a fifth gap or interstice 40 between the fifth strut row 20 and the sixth strut row 20, and a sixth plurality of connectors 22 extending across a sixth gap or interstice 40 between the sixth strut row 20 and the seventh strut row 20.

The length of the gap or interstice 40 between adjacent strut rows 20 for one or more of the intermediate plurality of connectors 22 may be greater than for the length of the gap or interstice 40 between an adjacent plurality of connectors 22. For example, the length of the third gap 40 and/or the fourth gap 40 (which may be the same or different) may be greater than the length of the first gap 40, second gap 40, fifth gap and/or the sixth gap 40.

At least some of the plurality of connectors 22 may define a flexible hinge portion 50 having a greater lateral flexibility than other portions of the expandable framework 12. For example, one or more of the intermediate plurality of connectors 22 (which may extend across a gap or interstice 40 having a length greater than an adjacent gap or interstice 40) may provide a flexible hinge portion 50. The flexible hinge portion 50 may be bounded by two opposing end portions of the expandable tubular framework 12 made up of one or more strut rows 20 and associated connectors 22. In at least some embodiments, the two end portions may have a greater stiffness than the flexible hinge portion 50.

Figure 6:
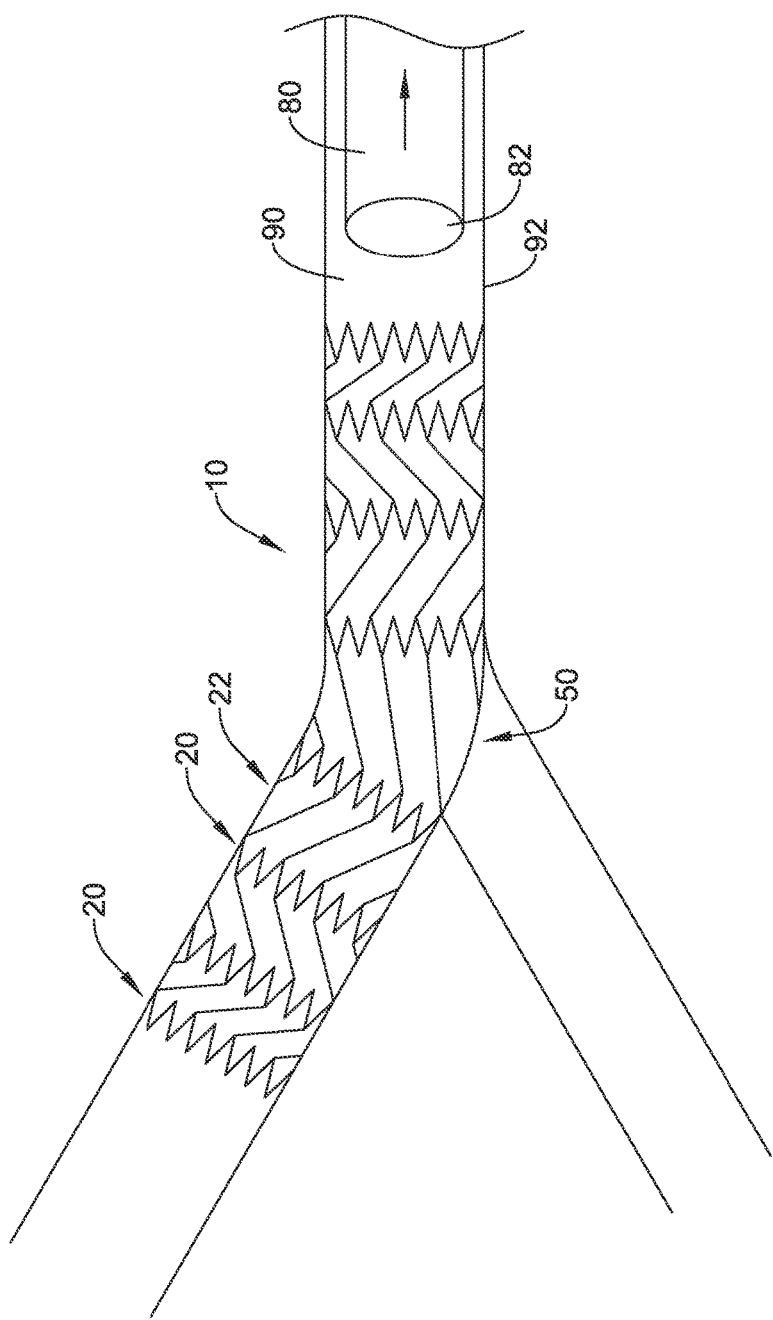
FIG. 6 illustrates aspects of delivering an example endoprosthesis according to FIGS. 1-5 into a body lumen.
Figure 7:
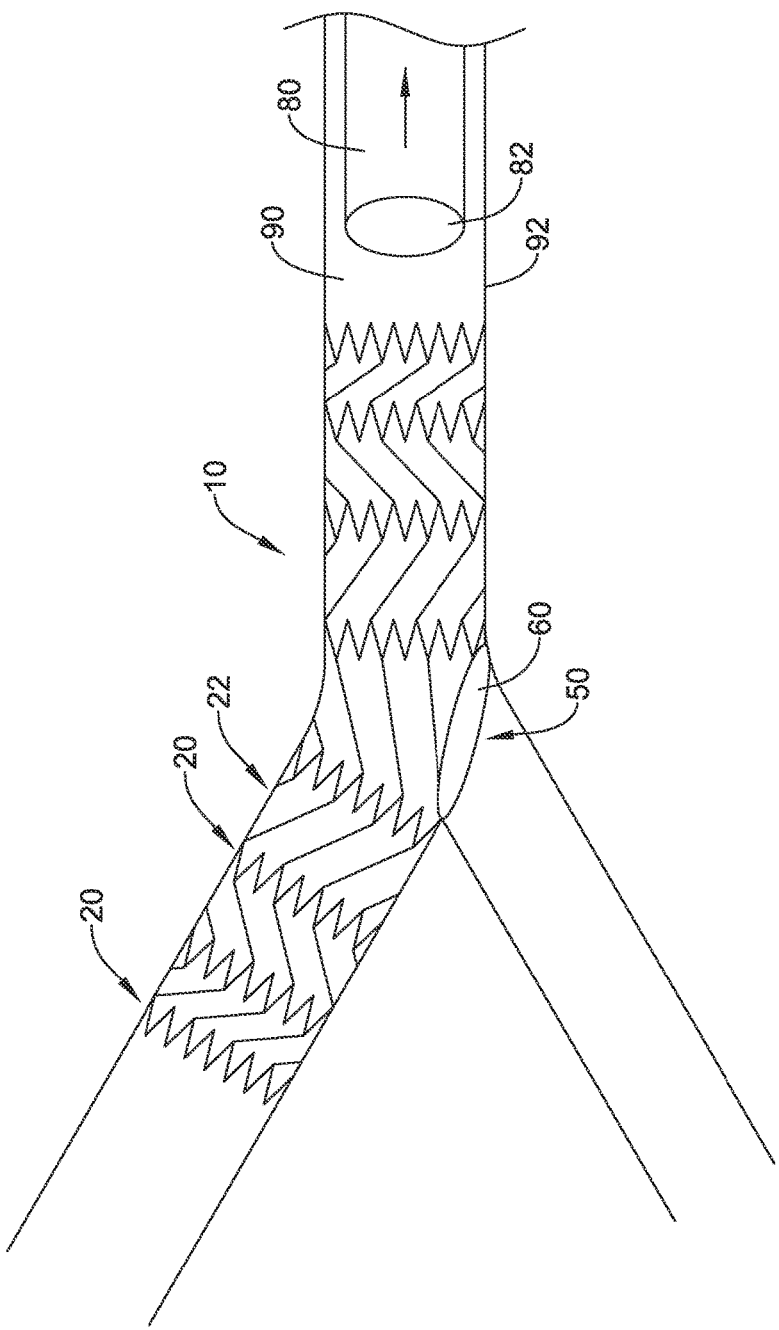
FIGS. 7-8 illustrate aspects of delivering an example endoprosthesis into a body lumen.
Figure 8:
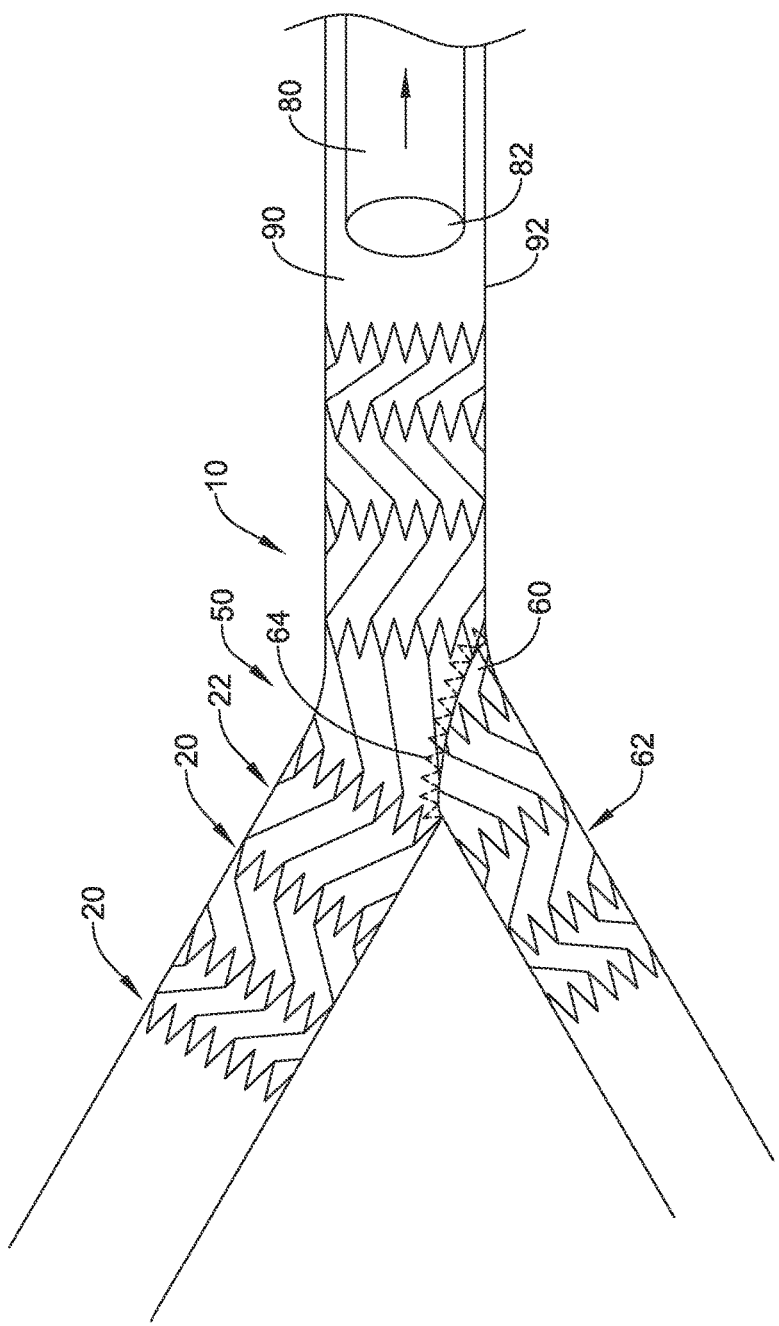

In use, it may be advantageous to place the endoprosthesis 10 such that the flexible hinge portion 50 of the expandable tubular framework 12 is disposed at or across a bend of a body lumen 90, as seen in FIGS. 6-8 for example. In some embodiments, the flexible hinge portion 50 may be adapted to maintain at least 60% patency of the lumen extending through the expandable tubular framework 12 when the expandable tubular framework 12 is bent at the flexible hinge portion 50. In some embodiments, the flexible hinge portion 50 may be adapted to maintain at least 70% patency of the lumen extending through the expandable tubular framework 12 when the expandable tubular framework 12 is bent at the flexible hinge portion 50. In some embodiments, the flexible hinge portion 50 may be adapted to maintain at least 80% patency of the lumen extending through the expandable tubular framework 12 when the expandable tubular framework 12 is bent at the flexible hinge portion 50. In some embodiments, the flexible hinge portion 50 may be adapted to maintain at least 90% patency of the lumen extending through the expandable tubular framework 12 when the expandable tubular framework 12 is bent at the flexible hinge portion 50. Accordingly, the flexible hinge portion 50 may resist collapse of the lumen and/or kinking of the expandable tubular framework 12, thereby providing increased and/or improved fluid flow therethrough around and/or across a bend in the body lumen 90.

Each of the plurality of connectors 22 has a connector length. In some instances, a first plurality of connectors may have a first connector length, a second plurality of connectors may have a second connector length, a third plurality of connectors may have a third connector length, a fourth plurality of connectors may have a fourth connector length, etc. In some instances, the second connector length may be greater than the first connector length. In some instances, the third connector length may be greater than the first connector length and/or the second connector length. In some instances, the third connector length may be less than the first connector length and/or the second connector length. In some instances, the fourth connector length may be greater than the first connector length, the second connector length, and/or the third connector length. In some instances, the fourth connector length may be less than the first connector length, the second connector length, and/or the third connector length.

In at least some embodiments, the connector length may be directly or indirectly related to the non-parallel angle relative to the central longitudinal axis of the angled segment 34. If the length of a gap or interstice 40 is held constant, the smaller or more acute the non-parallel angle is relative to the central longitudinal axis, the shorter the connector length may be. In some instances, a longer connector length may permit a plurality of connectors 22 to skip one or more additional peaks 24 before connecting to an adjacent strut row 20. In some instances, a longer connector length may correspond to an increased length of a gap or interstice 40. In some instances, a longer connector length and/or an increased length of a gap or interstice 40 may provide enhanced flexibility to the plurality of connectors 22 and/or the flexible hinge portion 50.

In some embodiments, the at least some of the plurality of connectors 22 may include some or all of one row or group of connectors extending between and interconnecting two adjacent strut rows 20 (e.g., the first plurality of connectors, the second plurality of connectors, and/or the third plurality of connectors, etc.). In some embodiments, the at least some of the plurality of connectors 22 may include more than one row or group of connectors extending between and interconnecting adjacent strut rows 20. In some embodiments, at least some of the plurality of connectors 22 of an endoprosthesis 10 may define more than one flexible hinge portion 50. In some embodiments, a flexible hinge portion 50 may further include an enlarged opening 60 passing through a side of the expandable tubular framework 12, as seen in FIG. 7, for example.

In some instances, an endoprosthesis 10 may include a second expandable tubular framework 62 configured to be positioned through a side of the expandable tubular framework 12 within an enlarged opening 60 in the flexible hinge portion 50, as seen in FIG. 8, for example. In some instances, when the second expandable tubular framework 62 is positioned through the side of the expandable tubular framework 12 within the enlarged opening 60, a first end portion of the second expandable tubular framework 62 is positioned or disposed within the lumen 18 of the expandable tubular framework 12. In some instances, when the second expandable tubular framework 62 is positioned through the side of the expandable tubular framework 12 within the enlarged opening 60, an opposing second end portion of the second expandable tubular framework 62 is positioned or disposed outside of the expandable tubular framework 12, such as in a lumen branching off of the body lumen 90 at a bifurcation. In some embodiments, the first end portion of the second expandable tubular framework 62 may include a circumferential ridge portion 64 configured to engage the expandable tubular framework 12 with the circumferential ridge portion 64 disposed inside of the expandable tubular framework 12. In some instances, the circumferential ridge portion 64 of the second expandable tubular framework 62 may have a greater maximum outer extent than the enlarged opening 60 in the flexible hinge portion 50 of the expandable tubular framework 12.

In some embodiments, the endoprosthesis 10 may include a polymeric cover 30, such as a polymeric coating. The polymeric cover 30 may be any desired polymeric coating, such as a polyurethane coating or silicone coating, for example. Other coatings and/or coating materials are also contemplated. In some instances, the polymeric cover 30 may include a therapeutic agent embedded therein, disposed thereon, etc., if desired.

In some instances, the endoprosthesis 10, such as a stent, may be considered a fully covered stent in which the polymeric cover 30 may extend a full length of the endoprosthesis 10 from the first end 14 to the second end 16. Thus, the polymeric cover 30 may cover the plurality of strut rows 20 including the interstitial spaces between the strut segments of the plurality of strut rows 20 and span the gaps or interstices 40 between adjacent strut rows 20. In some instances, the polymeric cover 30 may cover all of the plurality of strut rows 20, including a first strut row, a second strut row, a third strut row, a fourth strut row, a fifth strut row, etc. and span the gaps or interstices 40 between the first strut row, the second strut row, the third strut row, the fourth strut row, the fifth strut row, etc. In other instances, the endoprosthesis 10, such as a stent, may be considered a partially covered stent in which the polymeric cover 30 may extend over a portion of the endoprosthesis 10. In some instances, the polymeric cover 30 may cover one or more of the plurality of strut rows 20 including the interstitial spaces between the strut segments of the plurality of strut rows 20 and/or span the gaps or interstices 40 between adjacent strut rows 20, but may cover less than all of the plurality of strut rows 20 and/or less than all of the gaps or interstices 40 between adjacent strut rows 20. For example, in some instances, the gaps or interstices 40 between adjacent strut rows 20 forming the flexible hinge portion 50 may be devoid of the polymeric cover 30. In some embodiments, the gaps or interstices 40 between adjacent strut rows 20 forming the flexible hinge portion 50 may be devoid of the polymeric cover 30 when the flexible hinge portion 50 includes an enlarged opening 60 and/or when the flexible hinge portion 50 is placed at a bifurcation in a body lumen.

In most instances, the polymeric cover 30 may not extend across some or all of the spaces or openings 28 between the plurality of connectors 22 and the plurality of strut rows 20. Thus, the spaces or openings 28 between the plurality of connectors 22 and the plurality of strut rows 20 to which the plurality of connectors 22 is interconnected with may be devoid of the polymeric cover 30 to permit tissue ingrowth around the plurality of connectors 22 and through the spaces or openings 28. For example, the spaces or openings 28 between a first plurality of connectors 22 and a first strut row and a second strut row may be devoid of the polymeric cover 30 and open (e.g., unobstructed) to permit tissue ingrowth therethrough, the spaces or openings 28 between a second plurality of connectors 22 and a second strut row and a third strut row may be devoid of the polymeric cover 30 and open (e.g., unobstructed) to permit tissue ingrowth therethrough, and the spaces or openings 28 between a third plurality of connectors 22 and a third strut row and a fourth strut rows may be devoid of the polymeric cover 30 and open (e.g., unobstructed) to permit tissue ingrowth therethrough, etc. Thus, the endoprosthesis 10 may provide the benefits of a fully covered endoprosthesis, while also providing resistance to migration as a result of tissue ingrowth.

In some embodiments, the plurality of connectors 22 extending between adjacent strut rows 20 may be exposed to permit tissue ingrowth around the plurality of connectors 22 and/or through the spaces or openings 28, while the polymeric cover 30 prevents tissue ingrowth around and/or through other portions of the endoprosthesis 10. Accordingly, subsequent to implantation of the endoprosthesis 10, tissue may grow around the plurality of connectors 22 and/or through the spaces or openings 28 to prevent migration of the implanted endoprosthesis 10. However, in the event that it is desired to remove or reposition the endoprosthesis 10 at a subsequent time after tissue ingrowth has occurred, the ingrown tissue can be cut away from the plurality of connectors 22 or the plurality of connectors 22 can be otherwise released from the ingrown tissue. Since the ingrown tissue is only located at discrete locations (e.g., at the plurality of connectors 22), the procedure for removing the endoprosthesis 10 may be less traumatic than if the tissue were ingrown throughout the entire expandable tubular framework 12 including the plurality of strut rows 20, such as with a bare or completely uncovered endoprosthesis.

If it is desired to coat the expandable tubular framework 12 with a polymeric cover 30, the polymeric cover 30 may be applied to the expandable tubular framework 12. For example, the expandable tubular framework 12 may be coated with a polymeric cover 30 by dipping the expandable tubular framework 12 into a reservoir of a polymeric material solution. In other instances, a polymeric material solution may be sprayed onto the expandable tubular framework 12, or otherwise applied to the expandable tubular framework 12.

In some embodiments, a layer of the polymeric material solution may be formed across the expandable tubular framework 12, covering the plurality of strut rows 20 and spanning the gaps or interstices 40 between adjacent strut rows 20, as well as the plurality of connectors 22 and the spaces or openings 28 between the plurality of connectors 22 and the plurality of strut rows 20 to which the plurality of connectors 22 is interconnected. It is noted that, in some instances, the layer of polymeric material solution may be applied to the expandable framework 12 while the expandable tubular framework 12 is positioned around a mandrel.

The expandable tubular framework 12, with a mandrel extending through the lumen of the expandable tubular framework 12, may then be subjected to a process for selectively removing the polymeric material solution from the spaces or openings 28 between the plurality of connectors 22 and the plurality of strut rows 20 to which the plurality of connectors 22 is interconnected while retaining the polymeric material solution covering the plurality of strut rows 20 and spanning the gaps or interstices 40 between adjacent strut rows 20. For example, a fluid (e.g., air) may be blown toward the spaces or openings 28 between the plurality of connectors 22 and the plurality of strut rows 20 to selectively remove the coating from the spaces or openings 28. For example, the membrane of the polymeric coating material extending across the spaces or openings 28 may be popped or ruptured by blowing the fluid toward the spaces or openings 28. The fluid (e.g., air) may be directed toward the spaces or openings 28 with one or more fluid nozzles, for example. The presence of the mandrel within the expandable tubular framework 12 may prevent the fluid from rupturing the membrane of the polymeric coating material spanning the gaps or interstices 40 between adjacent strut rows 20, thus retaining the coating covering the plurality of strut rows 20 and spanning the gaps or interstices 40 between adjacent strut rows 20. In other instances, the polymeric coating material extending across the spaces or openings 28 may be mechanically popped or ruptured, or the surface tension of the polymeric coating material extending across the spaces or openings 28 may be modified, such as chemically modified, to pop or rupture the polymeric coating material extending across the spaces or openings 28. In other instances, the polymeric coating material may be prevented from spanning the spaces or openings 28 between the plurality of connectors 22 and the plurality of strut rows 20 while retaining the coating covering the plurality of strut rows 20 and spanning the gaps or interstices 40 between adjacent strut rows 20. For example, the spaces or openings 28 may be masked off prior to applying the polymeric coating material and then subsequently removed, or the plurality of connectors 22 may be pre-treated, such as coated with a material, preventing wetting of the polymeric coating material across the spaces or openings 28 when applying the polymeric coating material.

In some instances, a single layer of the polymeric coating may be applied to form the polymeric cover 30. In other instances, multiple layers of the polymeric coating may be applied to form the polymeric cover 30. The coating extending across the spaces or openings 28 may be ruptured after each layer of the coating is applied or after multiple layers of the coating have been applied. For example, fluid may be blown toward the spaces or openings 28 to rupture the coating extending across the spaces or openings 28 after each layer of the coating is applied, or after multiple layers of the coating have been applied.

The polymeric material solution coating the expandable tubular framework 12 may then be cured to form the polymeric cover 30 disposed on the expandable tubular framework 12. In some instances, the polymeric cover 30 may extend the entire length of the expandable tubular framework 12. In other instances, the polymeric cover 30 may extend along only a portion of the length of the expandable tubular framework 12, if desired.

FIGS. 6 and 7 illustrate selected aspects of delivering an endoprosthesis 10 into a body lumen. The endoprosthesis 10 may be advanced in a compressed state within a tubular sheath 80 to a target location within a body lumen 90, such as a body lumen of the vascular, urinary, biliary, tracheobronchial, esophageal or renal tracts. Once positioned at a desired location, the endoprosthesis 10 may be deployed from the distal opening 82 at the distal end of the delivery sheath 80. For example, the delivery sheath 80 may be moved proximally relative to the endoprosthesis 10 such that the endoprosthesis 10 is deployed from the distal opening 82, as seen in FIG. 6.

A distalmost of the plurality of strut rows 20 may be expelled from the distal end of the tubular sheath 80, followed by the remainder of the strut rows 20 of the endoprosthesis. In some embodiments, once the distalmost strut row 20 exits the distal opening 82 of the delivery sheath 80, the distalmost strut row 20 may automatically expand toward its expanded state and press against a wall 92 of the body lumen 90. The plurality of connectors 22 may be of sufficient length such that the distalmost strut row 20 may expand against the wall 92 of the body lumen 90 while an adjacent strut row 20 may remain in a compressed state within the delivery sheath 80. The distalmost strut row 20 may only expand to the expanded state once the entire distalmost strut row 20 is expelled from the tubular sheath 80.

Subsequent strut rows 20 of the endoprosthesis 10 may be deployed from the delivery sheath 80 in a similar manner. For example, each of the plurality of strut rows 20 may remain in the compressed state until the entire strut row 20 is expelled from the distal end of the tubular sheath 80. Thus, each of the plurality of strut rows 20 may expand independent of adjacent strut rows 20 and the expansion of one of the plurality of strut rows 20 does not cause any jumping effect of adjacent strut rows 20 emerging from the delivery sheath 80.

Similar to the other strut rows 20, a proximalmost strut row 20 may remain in the compressed state until the entire proximalmost strut row 20 is expelled from the distal end of the tubular sheath 80. Thus, unlike other expandable endoprostheses in which expansion of the endoprosthesis tends to cause adjacent strut rows to "jump" out of the delivery sheath 80 uncontrollably, the endoprosthesis 10 of the present disclosure may allow for precise and controlled placement of the endoprosthesis 10 in the body lumen 90.

Furthermore, the stepped deployment of the endoprosthesis 10 may provide tactile feedback to the operator as each of the plurality of strut rows 20 is expelled from the distal opening 82 of the delivery sheath 80. For example, a snapping effect or pulse generated at the moment one of the plurality of strut rows 20 is fully exposed from the delivery sheath 80 and exits the delivery sheath 80 entirely may translate down the delivery sheath 80 to the operator and may allow the operator to feel when each of the plurality of strut rows 20 has expanded in the body lumen 90.

In some embodiments, an endoprosthesis 10 may be deployed at a bifurcation in a body lumen 90. In some instances, a flexible hinge portion 50 of an elongate tubular framework 12 may be deployed at the bifurcation to permit the endoprosthesis 10 to bend without collapsing, kinking, or otherwise reducing the patency of the body lumen 90 of the body lumen 90. In some embodiments, the flexible hinge portion 50 may be devoid of a polymeric cover 30, thereby permitting fluid flow through the bifurcation. In some embodiments, the flexible hinge portion 50 may include an enlarged opening 60 through a side of the expandable tubular framework 12. The enlarged opening 60 may be placed, disposed, and/or deployed at the bifurcation. In some instances, the enlarged opening 60 may be devoid of a polymeric cover 30 and/or may permit fluid flow through the bifurcation.

In some instances, it may be beneficial to deploy a second expandable tubular framework 62 within a lumen branching off from the body lumen 90 at the bifurcation, as illustrated in FIG. 8, for example. In some embodiments, the second expandable tubular framework 62 may be disposed within the delivery sheath 80 proximal of the expandable tubular framework 12. After deploying the expandable tubular framework 12 as described above, the delivery sheath 80 may be advanced within the deployed endoprosthesis 10 to the bifurcation in the body lumen 90, where the second expandable tubular framework 62 may be deployed through the enlarged opening 60 and into the lumen branching off from the body lumen 90 by in a similar manner to the expandable tubular framework 12 described above. The second expandable tubular framework 62 may include a circumferential ridge portion 64 at a first, proximal end of the second expandable tubular framework 62. The circumferential ridge portion 64 may be engaged with and/or against the expandable tubular framework 12.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims. This may include, to the extent that it is appropriate, the use of any of the features of one example embodiment or aspect being used in other embodiments or aspects.

What is claimed is:

1. An endoprosthesis, comprising:
an expandable tubular framework having a first end and a second end defining a length therebetween, and a lumen extending therethrough along a central longitudinal axis, the expandable tubular framework being expandable from a compressed state to an expanded state and including:
 a plurality of strut rows including at least a first strut row, a second strut row, a third strut row, and a fourth strut row, each strut row having alternating peaks located toward the first end and valleys located toward the second end;
 a first plurality of connectors extending across a first gap defined between valleys of the first strut row and peaks of the second strut row, the first plurality of connectors interconnecting peaks of the first strut row and peaks of the second strut row, the first gap having a first length;

a second plurality of connectors extending across a second gap defined between valleys of the third strut row and peaks of the fourth strut row, the second plurality of connectors interconnecting peaks of the third strut row and peaks of the fourth strut row, the second gap having a second length; and a third plurality of connectors extending across a third gap defined between valleys and peaks of adjacent strut rows intermediate the first plurality of connectors and the second plurality of connectors, the third plurality of connectors interconnecting peaks of the adjacent strut rows defining the third gap therebetween, the third gap having a third length;

wherein the plurality of strut rows defines an outer diameter in the expanded state;

wherein at least one of the first plurality of connectors, the second plurality of connectors, and the third plurality of connectors extends radially outward beyond the outer diameter in the expanded state;

wherein the third length is greater than the first length and the second length.

2. The endoprosthesis of claim 1, wherein the third plurality of connectors interconnect peaks of the second strut row and peaks of the third strut row.

3. The endoprosthesis of claim 2, wherein the first plurality of connectors extends in a first helical direction, the third plurality of connectors extends in a second helical direction opposite the first helical direction, and the second plurality of connectors extends in the first helical direction.

4. The endoprosthesis of claim 1, further comprising a fourth plurality of connectors extending across a fourth gap defined between valleys and peaks of adjacent strut rows intermediate the first plurality of connectors and the second plurality of connectors, the fourth plurality of connectors interconnecting peaks of the adjacent strut rows defining the fourth gap therebetween, the fourth gap having a fourth length;

wherein the fourth length is greater than the first length and the second length.

5. The endoprosthesis of claim 1, further comprising a polymeric cover covering the plurality of strut rows and spanning the first, second, and third gaps;

wherein spaces between the first plurality of connectors and the first strut row and the second strut row are devoid of the polymeric cover and open to permit tissue ingrowth therethrough;

wherein spaces between the second plurality of connectors and the third strut row and the fourth strut row are devoid of the polymeric cover and open to permit tissue ingrowth therethrough; and wherein spaces between the third plurality of connectors and the adjacent strut rows interconnected thereto are devoid of the polymeric cover and open to permit tissue ingrowth therethrough.

6. An endoprosthesis, comprising:

an expandable tubular framework having a first end and a second end defining a length therebetween, and a lumen extending therethrough along a central longitudinal axis, the expandable tubular framework being expandable from a compressed state to an expanded state and including:

a plurality of strut rows including at least a first strut row, a second strut row, a third strut row, and a fourth strut row, each strut row including alternating peaks located toward the first end and valleys located toward the second end;

a first plurality of connectors extending across a first gap defined between valleys of the first strut row and peaks of the second strut row, the first plurality of connectors interconnecting peaks of the first strut row and peaks of the second strut row, the first gap having a first length;

a second plurality of connectors extending across a second gap defined between valleys of the third strut row and peaks of the fourth strut row, the second plurality of connectors interconnecting peaks of the third strut row and peaks of the fourth strut row, the second gap having a second length; and a third plurality of connectors extending across a third gap defined between valleys and peaks of adjacent strut rows intermediate the first plurality of connectors and the second plurality of connectors, the third plurality of connectors interconnecting peaks of the adjacent strut rows defining the third gap therebetween, the third gap having a third length, wherein the third length is greater than the first length and the second length such that the third plurality of connectors define a flexible hinge portion.

7. The endoprosthesis of claim 6, wherein the flexible hinge portion is between first and second end portions of the expandable tubular framework, the first end portion including the first and second strut rows and the first plurality of connectors therebetween, the second end portion including the third and fourth strut rows and the second plurality of connecters therebetween.

8. The endoprosthesis of claim 6, further comprising a polymeric cover covering the plurality of strut rows and spanning the first, second, and third gaps;

wherein spaces between the first plurality of connectors and the first strut row and the second strut row are devoid of the polymeric cover and open to permit tissue ingrowth therethrough;

wherein spaces between the second plurality of connectors and the third strut row and the fourth strut row are devoid of the polymeric cover and open to permit tissue ingrowth therethrough; and wherein spaces between the third plurality of connectors and the adjacent strut rows interconnected thereto are devoid of the polymeric cover and open to permit tissue ingrowth therethrough.

\* \* \* \* \*